(12) United States Patent
Koski et al.

(10) Patent No.: US 8,165,661 B2
(45) Date of Patent: Apr. 24, 2012

(54) METHOD AND APPARATUS FOR ANALYZING AMNIOTIC FLUID

(75) Inventors: Kristine G. Koski, Montréal (CA); David H. Burns, Montréal (CA)

(73) Assignee: McGill University, Montreal (CA)

(*) Notice: Subject to any disclaimer, the term of this patent is extended or adjusted under 35 U.S.C. 154(b) by 1179 days.

(21) Appl. No.: 10/568,674

(22) PCT Filed: Aug. 21, 2004

(86) PCT No.: PCT/IB2004/002720
§ 371 (c)(1), (2), (4) Date: Feb. 17, 2006

(87) PCT Pub. No.: WO2005/019792
PCT Pub. Date: Mar. 3, 2005

(65) Prior Publication Data
US 2006/0247536 A1  Nov. 2, 2006

Related U.S. Application Data

(60) Provisional application No. 60/496,884, filed on Aug. 21, 2003.

(51) Int. Cl.
*A61B 8/00* (2006.01)
(52) U.S. Cl. ........ 600/473; 600/407; 600/475; 600/476; 600/477; 600/478; 382/128; 382/130; 382/131
(58) Field of Classification Search ............... 600/323, 600/309, 338, 407, 437, 473, 475, 476, 477, 600/478; 324/309; 382/128; 709/19, 20, 709/23
See application file for complete search history.

(56) References Cited

U.S. PATENT DOCUMENTS

| | | | |
|---|---|---|---|
| 5,172,693 A | 12/1992 | Doody | |
| 5,235,985 A | 8/1993 | McMorrow et al. | |
| 5,856,196 A * | 1/1999 | Alvarez et al. | 436/71 |
| 6,044,284 A | 3/2000 | Eisenfeld et al. | |
| 6,618,138 B2 * | 9/2003 | Khoury | 356/302 |
| 6,683,455 B2 * | 1/2004 | Ebbels et al. | 324/309 |
| 6,690,958 B1 * | 2/2004 | Walker et al. | 600/323 |
| 7,191,068 B2 * | 3/2007 | Rosenfeld et al. | 702/19 |
| 7,399,278 B1 * | 7/2008 | Ross | 600/437 |

(Continued)

FOREIGN PATENT DOCUMENTS

GB  2269007  1/1994

(Continued)

OTHER PUBLICATIONS

English Abstract of JP 2004-121733, Apr. 22, 2004.

(Continued)

*Primary Examiner* — Tse Chen
*Assistant Examiner* — Baisakhi Roy
(74) *Attorney, Agent, or Firm* — Bereskin & Parr/S.E.N.C.R.L., s.r.l.

(57) ABSTRACT

Methods and spectra for monitoring fetal growth and predicting birth weight of an infant prior to birth are provided wherein one or more selected biological markers are measured in a sample of amniotic fluid obtained from a pregnant woman. Levels of the selected biochemical markers and/or spectra correlate with one or more medical conditions, such as fetal growth and birth weight of the infant, and gestational diabetes. A measurement probe for in situ measurement can be used safely and repeatedly. Monitoring and/or treatment of maternal and fetal health is also provided.

21 Claims, 8 Drawing Sheets

U.S. PATENT DOCUMENTS

| | | | |
|---|---|---|---|
| 7,515,948 B1* | 4/2009 | Balberg et al. | 600/323 |
| 7,524,681 B2 | 4/2009 | Wolf et al. | |
| 2004/0024302 A1 | 2/2004 | Chalana et al. | |
| 2004/0197930 A1* | 10/2004 | Rosenfeld et al. | 436/510 |
| 2004/0267139 A1 | 12/2004 | Kanayama et al. | |
| 2005/0266405 A1* | 12/2005 | Kopreski | 435/6 |

FOREIGN PATENT DOCUMENTS

| | | |
|---|---|---|
| JP | S62215398 | 9/1987 |
| JP | H5203644 | 8/1993 |
| JP | 2003144439 | 5/2003 |
| JP | 2004121733 | 4/2004 |
| JP | 2004520584 | 7/2004 |
| JP | 2007-504883 | 3/2007 |
| JP | 2007506979 | 3/2007 |
| WO | 8802616 | 4/1988 |
| WO | 9107910 | 6/1991 |
| WO | 9200699 | 1/1992 |
| WO | 9503738 | 2/1995 |
| WO | 9717884 | 5/1997 |
| WO | 9718749 | 5/1997 |
| WO | 9940842 | 8/1999 |
| WO | 2004036359 | 4/2004 |
| WO | 2005025399 | 3/2005 |

OTHER PUBLICATIONS

English Abstract of JP 2003-144439, May 20, 2003.
European Search Report dated May 2, 2008 for European Patent Application No. 04786402.0.
European Office Action dated Oct. 1, 2009 for European Patent Application No. 04786402.0.
Chinese Office Action and English Translation dated Jul. 11, 2008 for Chinese Patent Application No. 200480044284.9.
Chinese Office Action and English Translation dated Dec. 26, 2008 for Chinese Patent Application No. 200480044284.9.
Australian Office Action dated May 25, 2010 for Australian Patent Application No. 2004267244.
Japanese Office Action and English Translation dated May 25, 2010 for Japanese Patent Application No. 2007-526581.
Petrovskii, "Portable photometer for determining bilirubin in amniotic fluid", Journal of Optical Technology, vol. 61, No. 12, pp. 909-911, Dec. 1994.
JP 2007-526581, Office Action mailed Feb. 8, 2011.

* cited by examiner

METHOD AND APPARATUS FOR ANALYZING AMNIOTIC FLUID

CROSS-REFERENCE TO RELATED APPLICATIONS

This application claims priority of U.S. provisional patent application Ser. No. 60/496,884 filed Aug. 21, 2003, the content of which is hereby incorporated by reference.

US FEDERAL GOVERNMENT SPONSORED RESEARCH

The inventions described and claimed in this application are not based on research funded by the US federal government or its agencies, and the US government has no rights to this patent application.

FIELD OF THE INVENTION

The present invention relates to methods and apparatus for determining fetal health or a risk of developing a fetal health condition. The invention also relates to methods and apparatus for monitoring maternal health. The invention further relates to methods and apparatus for analyzing amniotic fluid to determine one or more biological markers.

BACKGROUND OF THE INVENTION

The assessment of fetal birth weight forms an important part of prenatal care. Therefore accurate early determination of fetal weight prior to delivery could markedly improving perinatal outcomes. Thus there is a need for a quick and easy method for estimating fetal weight in-utero particularly infants at risk of for either of the two extremes: (1) macrocosmia (also referred to as large for gestational age or LGA) or (2) small for gestational age (SGA) or intrauterine growth retarded (IUGR).

Currently the most reliable predictor of infant birth weight is ultrasonography where according to a recent review article it is capable of predicting birth weight to within 300 to 400 grams (Table 12, Nahum eMedicine Journal), but the authors cited that this as well as other techniques still have significant degrees of inaccuracy and suggested that a reasonable strategy for arriving at estimated fetal weight is still to use multiple estimates based on different sources of clinical and sonographic information. Moreover they noted that even with ultrasound, macrosomia is not easily predicted. Both ultrasonography and clinical palpation of fetal size have sensitivities of less than 60% for the prediction of macrosomia with false positives far greater than 40%. Likewise for small fetuses less than 1800 grams ultrasonic fetal weight estimates are often in error by as much as 25%. The disadvantages of ultrasonography include the complicated and labor intensive nature of the methodology that is often limited by the suboptimal visualization of fetal organs. It also requires costly equipment and highly trained personnel. The latter requisites often preclude use of any of current techniques in developing countries.

The use of ultrasound measurements of the fetus and information about the mother are combined to determine birth weight in WO2004/036359 published on 29 Apr. 2004.

Current American and Canadian guidelines recommend that all pregnant women be screened for gestational diabetes mellitus (GDM) between 24-28 weeks. Prior screening occurs only if multiple risk factors such as older maternal age, higher pre-pregnancy weight, membership in a high risk ethnic group or strong family history of diabetes exist or if previous diagnosis of GDM or delivery of macrosomic infant have occurred. However, several studies acknowledge that 'selective screening' based on these criteria can still result in under-diagnosis of GDM.

Current screening and diagnostic criteria for GDM are predicated on the observation that an abnormal oral glucose tolerance test (OGTT), with its accompanying gestational hyperglycemia, increases both perinatal and adult morbidity and mortality. It is argued that the increased flux of glucose across the placenta is the stimulus for the in-utero production of insulin from developing pancreatic islet cells and is the precondition for fetal hyperinsulinism, which in turn leads to increased fetal abdominal circumference, macrosomia, obesity and neonatal hypoglycemia and the diagnosis of GDM.

SUMMARY OF THE INVENTION

According to one broad aspect of the invention, amniotic fluid is analyzed in situ without disrupting the amniotic sac.

According to another broad aspect of the invention, amniotic fluid is analyzed without altering the composition of the amniotic fluid, so as to ascertain information about concentration and/or other components of the matrix making up the fluid.

According to yet another broad aspect of the invention, analysis of amniotic fluid is correlated with a risk of developing a medical condition in at least one of a mother and her offspring.

According to a further broad aspect of the invention, prediction of birth weight from amniotic fluid analysis is improved either by providing prediction earlier during pregnancy or by providing better accuracy in the prediction.

The invention provides a method of analyzing amniotic fluid in which a device is provided for measuring one or more selected biological markers in amniotic fluid, and is arranged with respect to an amniotic sac to measure amniotic fluid in situ without insertion of any instrument into the amniotic sac. The device is used to acquire measurement data that is processed to obtain a value for one or more selected biological markers in the amniotic fluid.

The invention provides an apparatus for analyzing amniotic fluid in situ in a pregnant patient having an amniotic sac containing amniotic fluid without insertion of any instrument into the amniotic sac. The apparatus comprises a device for measuring one or more selected biological markers in amniotic fluid, a coupler adapted to arrange the device with respect to the amniotic sac to measure the amniotic fluid in situ without insertion of any instrument into the amniotic sac, and a processing unit for processing measurement data from the device to obtain a value for the one or more selected biological markers in the amniotic fluid.

The invention provides a method of treating at least one of pregnant mother and her fetus by providing a device for measuring one or more selected biological markers in amniotic fluid, arranging the device with respect to an amniotic sac to measure amniotic fluid in situ without insertion of any instrument into the amniotic sac, using the device to acquire measurement data, processing the measurement data to obtain a value for the one or more selected biological markers in the amniotic fluid, and determining at least one of a dietary change and a pharmaceutical intervention in response to the value.

The invention provides a method of predicting a risk of developing a medical condition in at least one of a mother and her offspring by providing a device for analyzing amniotic fluid of the mother, using the device to acquire analytical data from the amniotic fluid, and processing the analytical data to obtain a prediction value for the risk.

The invention provides an apparatus for predicting a risk of developing a medical condition in at least one of a mother and her offspring. The apparatus comprises a device for analyzing amniotic fluid, and a processing unit for processing analytical data from the device to obtain a prediction value for the risk.

The present invention may be applied to any animal having an amniotic fluid sac that allows for the fluid to be accessed for analysis, and in particular, the invention may be applied to humans. The terms "patient", "mother", "offspring", "fetus" and other similar terms relating to subjects and their body parts are intended herein to relate to humans and non-humans, unless otherwise explicitly indicated.

In this specification, the term "medical condition" means a condition that is, or has a probability to be, related to the health of mother, fetus or offspring. One example is weight of the offspring at the time of birth, namely birthweight, weight of the fetus such as small-for-gestational-age (SGA) or intrauterine growth retarded (IUGR), appropriate-for-gestational-age (AGA) or healthy, and large-for-gestational-age (LGA) or macrosomic. Abnormal weight is recognized be the cause of a variety of health complications. "Medical condition" also includes an indication of an absence of a problem such as AGA, which information to a pregnant woman is a reassurance having a benefit to the well-being of the mother. Another example is diabetes in the mother, otherwise known as maternal diabetes and more specifically, gestational diabetes mellitus (GDM). A further example is prematurity of birth.

In this specification, the term "biological marker" includes one or more biochemical indices such as glucose, lactate or another metabolic acid, one or more proteins that include but are not limited to insulin, insulin like growth factors (IGFs) and their binding proteins and/or one or more fatty acids. A biological marker may also comprise cells that can be identified and counted within the amniotic fluid, as well as other physical properties of amniotic fluid, such as viscosity, that can be measured, whether in vitro or in situ.

BRIEF DESCRIPTION OF THE DRAWINGS

The invention will be better understood by way of the following detailed description of several embodiments with reference to the appended drawings, in which.

DETAILED DESCRIPTION OF EMBODIMENTS

Figure 1A:
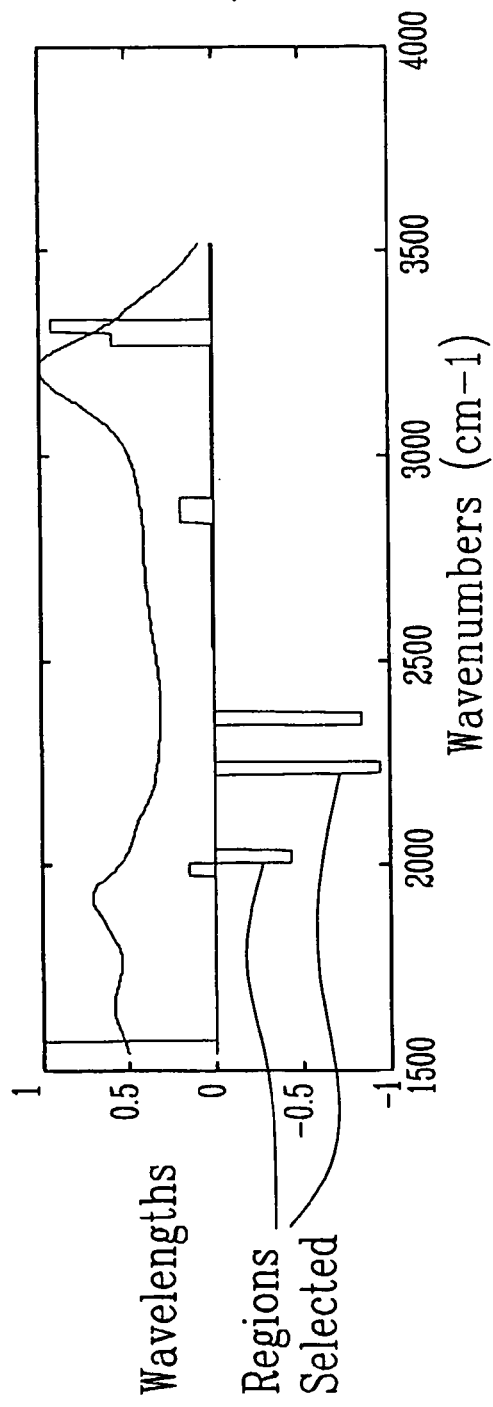
FIG. 1a illustrates the typical spectrum and wavelength regions selected for birthweight estimation using NIR Raman measurement of amniotic fluid for the broad range of birthweight ranging from 1 kg to 5.3 kg.

First Embodiment—NIR Raman Spectral Analysis of In Vitro Amniotic Fluid and Correlation with Birthweight in Humans One embodiment of the invention focuses on the use of Raman spectral analyses to identify a panel of 8-12 biochemical markers in amniotic fluid that are predictive of infant birth weight. Advantages of our approach are (1) that it requires a single sample of a small volume of amniotic fluid (µL) to measure all important biochemical components simultaneously and thus importantly preserves their chemical properties within the fluid matrix of amniotic fluid, which in and of itself is important barometer of fetal health as either too little (oligiohydramniois) or too much (polyhydramniois) is a fetal health risk. This overcomes limitations of other chemical techniques that require separate analyses of individual components, which not only are susceptible to concentration differences if volume is perturbed, but to lack of techniques to measure components in this new compartment for which assays in small volumes have not yet been developed. However more importantly, our Raman spectral analysis is accurate to within 100 to 400 grams of final birth weight when performed as early as 15 wks gestation. This thus provides the first medical possibility of early in-utero diagnosis of SGA and LGA. Moreover the methodology can be performed at the time of routine amniocentesis and does not require additional labor-intensive chemical processing of samples. The method of the present embodiment can be easily conducted in the hospital, clinic and field setting with the development of two machines: one requiring use of a small portable Raman spectrometer to measure amniotic fluid droplets at the time of collection of 'fresh samples' for immediate bedside processing and (2) the development of an endo-vaginal or an abdominal fibre optic probe to be used non invasively throughout the course of pregnancy providing for the first time a means to collect series measurements and to monitor in-utero fetal growth and development sequentially The feasibility of the method of the present embodiment makes the possibility of more widespread use of amniotic fluid for routine fetal monitoring possible and affordable and with an accuracy far exceeding current techniques.

The present applicants have identified several components of amniotic fluid suitable for measurement. These include but are not limited to glucose, a family of proteins including but not limited to insulin and two IGF binding proteins, namely IGF BP 1 and 3, several amino acids, and two metabolic acids (lactic acid and uric acid). Other components for measurement include nitric oxide and several fatty acids including the trans fatty acids which are only found in highly hydrogenated food products and that could in fact limit the use of the essential fatty acids required for fetal growth.

Amniotic Fluid NIR-RAMAN Spectroscopy

Amniotic fluid from 68 women at 14-16 weeks gestation, were measured. All patients signed McGill University a Human Subjects Approved form for consent. After genetic testing, all remaining amniotic samples were stored frozen. Near Infrared Raman spectral were obtained using a Bruker Fourier Transform Near Infrared Raman Spectrometer. Each amniotic fluid sample was taken from the freezer and warmed to 20 C. Samples were then transferred into a 2 mm diameter glass tube which and placed into the Raman system. The Raman system was maintained at 20+/−1 C during the course of the experiment. A Nd:YAG laser emitting at 1064 nm was focused onto the amniotic fluid samples. Raman shifted scattering from the samples was collected by the FT-spectrometer and detected using a cooled NIR detector. The spectra were scanned at 1/sec resulting in an 8 cm-1 resolution of shift from 0-3750 cm-1. A total of 1800 scans were averaged for each sample. After a Fourier Transform of the raw interferogram, the data was stored as 1919 data points spanning the 0-3750 cm-1 spectral range.

Data Preprocessing

The amniotic fluid RAMAN spectra were preprocessed to reduce the effects of intensity variations of the laser. In particular, each spectrum was normalized to the Raman emission of the Si—OH at 2500 cm-1. Likewise, spectra were smoothed with a 15-point moving average boxcar smoothing function to reduce spurious noise in the measurement.

Haar Transform

The Haar transform (HT) is the oldest form of wavelet analysis. It projects a given signal onto an orthogonal set of basis functions. Data contained in a time window of $0<\tau<1$ is decomposed according to a father wavelet $\phi(\tau)$, a mother wavelet $\psi(\tau)$ and a series of daughter wavelets $\psi_{n,k}(\tau)$, where n and k determine scaling and translation respectively:

$$\phi(\tau) = \begin{cases} 1 & \text{if } 0 \leq \tau \leq 1 \\ 0 & \text{otherwise} \end{cases} \quad (1)$$

$$\psi(\tau) = \begin{cases} 1 & \text{if } 0 \leq \tau \leq 1/2 \\ -1 & \text{if } 1/2 \leq \tau \leq 1 \\ 0 & \text{otherwise} \end{cases} \quad (2)$$

$$\psi_{n,k}(\tau) = \psi(2^n \tau - k), 0 \leq k \leq 2^n - 1 \quad (3)$$

Likewise, each daughter wavelet can be decomposed into the sum of two son wavelets, $\phi_{nk}(\tau)$, with a corresponding positive and negative weighting with the associated scaling and translation. It is interesting to note that all daughter wavelets can be decomposed into a sum of son wavelets, i.e. compressed and shifted versions of the father wavelet. For instance, $\psi = \phi_{1,0} - \phi_{1,1}$. Thus, the HT can be carried out with a basis set composed only of zeros and ones, which can be implemented experimentally by spectral filters. To determine the wavelet coefficients, it is useful to represent the wavelets by a matrix. For example, the father, mother and first generation of daughter wavelets can be written as $A_2$:

$$\begin{array}{cccc} \phi(\tau) & \psi(\tau) & \psi_{1,0}(\tau) & \psi_{1,1}(\tau) \end{array} \quad (4)$$

$$A_2 = \begin{bmatrix} 1 & 1 & 1 & 0 \\ 1 & 1 & -1 & 0 \\ 1 & -1 & 0 & 1 \\ 1 & -1 & 0 & -1 \end{bmatrix}$$

where each column corresponds to a wavelet, and each row represents the Haar wavelet values when the time window is broken into 4 equal segments. Decomposing a Raman signal of 4 equal wavenumber bins into wavelet coefficients is thus reduced to the following matrix math problem: a coefficient vector must be calculated such that its multiplication to $A_2$ yields the Raman spectral profile. Wavelet coefficients in the resulting vector will be ordered starting from the lowest resolution wavelet (father wavelet) and progressing to higher spectral resolution. Matrix $A_2$ can be expanded to include further generations of daughter wavelets or son wavelets, thereby extending the analysis to higher frequency levels.

More in-depth information on the Haar transform can be found in A. Graps, "An Introduction to Wavelets," IEEE Comput. Sci. Eng. 2, 50-61 (1995), E. Aboufadel and S. Schlicker, *Discovering Wavelets* (John Wiley & Sons Inc., NY, 1999), and in J. S. Walker, *A Primer on Wavelets and their Scientific Applications* (Chapman & Hall, Boca Raton, 1999).

Computing the Haar coefficients of the distributions collected experimentally using the FTNIR Raman instrument was the first step in the data analysis. The son wavelete Haar transform calculation was carried out by a custom program written in Matlab (The MathWorks Inc., Natick, Mass.) which iteratively calculated sums and differences. Computation required the length of the input data to be a power of 2 long. Coefficients for a maximum of 1024 Haar son wavelets were obtained, ordered from low resolution to high spectral resolution.

Stepwise Multilinear Regression

Inverse least squares regressions can be used to estimate the extrinsic parameters of a given sample from the preprocessed Raman spectra. However, it is probable that not all 1024 wavelets are needed, since the HT gives a sparse representation of the signal. The stepwise multilinear algorithm is an established method of choosing the subset of variables most correlated to a quantity of interest. The general goal of the genetic algorithm was to identify the combination of wavelets that best describes a given data set according to equation 5:

$$Y = \alpha_0 + \alpha_1 X_1 + \alpha_2 X_2 + \ldots \alpha_n X_n \quad (5)$$

where Y is the dependent variable (Birthweight), $X_1$, $X_2$, ..., $X_n$ are independent variables (i.e. wavelet coefficients), and $\alpha_0$, $\alpha_1$, ..., $\alpha_n$ are the coefficients determined from a set of X's by inverse least squares regression. The combination of wavelets that best estimated Y were determined according to the following scheme:

1. Set the range of HT coefficients that the Stepwise uses.
2. Choose the number of wavelets to include in the model.
3. Evaluate the fitness of each model.
4. Repeat steps 2-4 with an increasing number of wavelets included in the model.
5. Choose the optimal number of variables.
6. Evaluate the model using an independent data set.
7. Repeat steps 1-6 changing the range of HT coefficients used by the Stepwise method.

1. Setting the range of HT coefficients that the Stepwise MLR uses: The goal of the STEPMLR was to determine a small subset of wavelets correlated to the birthweight. Likewise, low-resolution (large wavelength range) components were preferable in view of developing identifying spectral components associated with fetal development and for simplified instrumentation in the future. Thus, in addition to allowing the Stepwise method to choose amongst all Haar son wavelets to optimize the estimation, the algorithm was also run with only wavelets of spectral resolution lower than 512, 256,128, 64 and 32 wavelets.

2. Choosing the number of wavelets to include in the model: Start with one wavelet, i.e. one X in equation 5, and increase progressively. The maximum number of wavelets was set according to the number of wavelet coefficients available for Stepwise selection. In all cases the maximum number of wavelets to use was set to 10.

3. Evaluating the fitness of each individual: For each model in the population, the coefficients $\alpha_1$ to $\alpha_n$ of equation 5 were calculated by inverse least squares regression using the calibration set with known values of absorption or scattering determined from sample preparation. Estimates of birthweight were obtained by applying equation 5 with the determined $\alpha_n$ parameters and the Haar coefficients of the test set, and a standard error of calibration (SEC) was calculated. Thus a smaller SEC was associated with a better model.

4. Repeat steps 2-3 with an increasing number of wavelets included in the model: The maximum number of wavelets was chosen in step 2.

5. Choosing the optimal number of variables: A prediction error sum of squares (PRESS) plot was generated by plotting SEC vs. the number of wavelets in the model. Let h designate the number of wavelets in the model with the minimum PRESS value. The model selected was the one with the fewest number of wavelets such that PRESS for that model was not significantly greater than PRESS for the model with h wavelets, based on an f-test at the 95% confidence level.[34]

6. Evaluating the model using an independent data set: The "optimal" model was evaluated by estimating the birthweight values of an independent data set, the validation set, with the calibration coefficients from the calibration set. $R^2$ and the coefficient of variation (C.V.) were used as indicators of the validity of the model.

Results

Figure 1B:
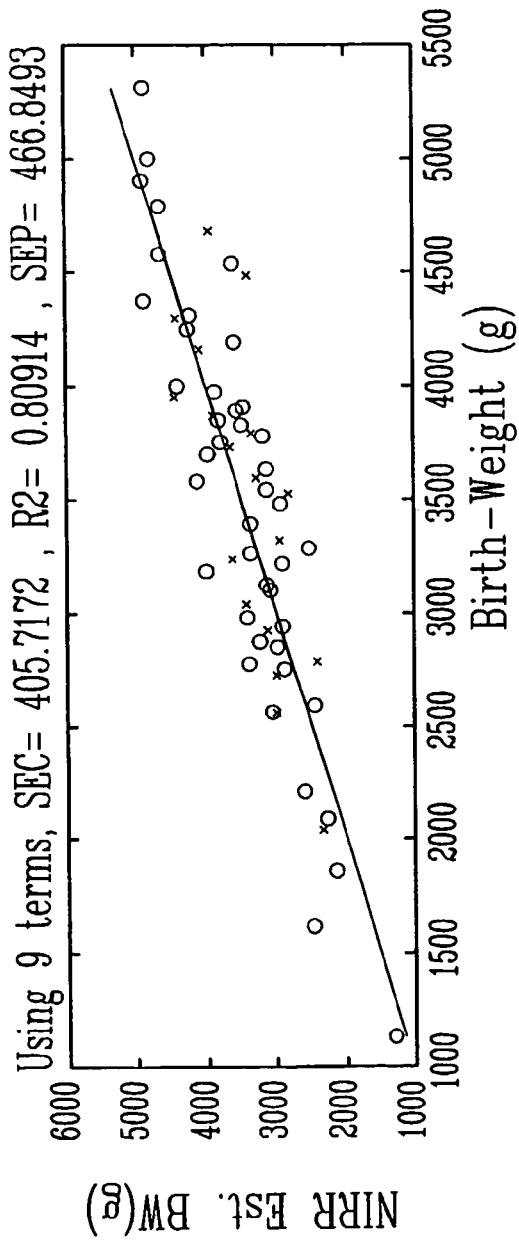
FIG. 1b illustrates the correlation fit between estimated birthweight and actual birthweight for the sample population for the broad range of birthweight ranging from 1 kg to 5.3 kg.
Figure 1C:
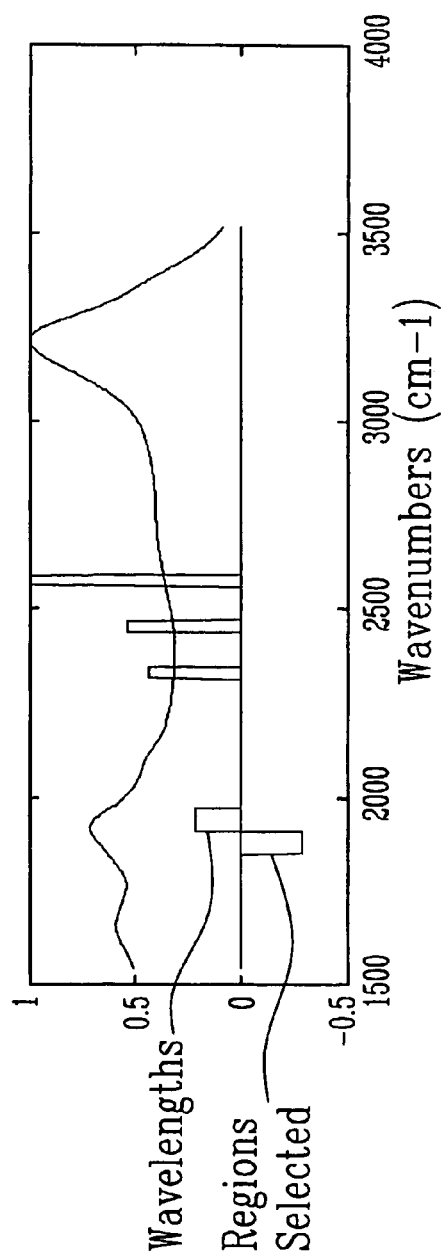
FIG. 1c illustrates the typical spectrum and wavelength regions selected for birthweight estimation using NIR Raman measurement of amniotic fluid for the lower range of birthweight ranging from 1 kg to 3.5 kg.
Figure 1D:
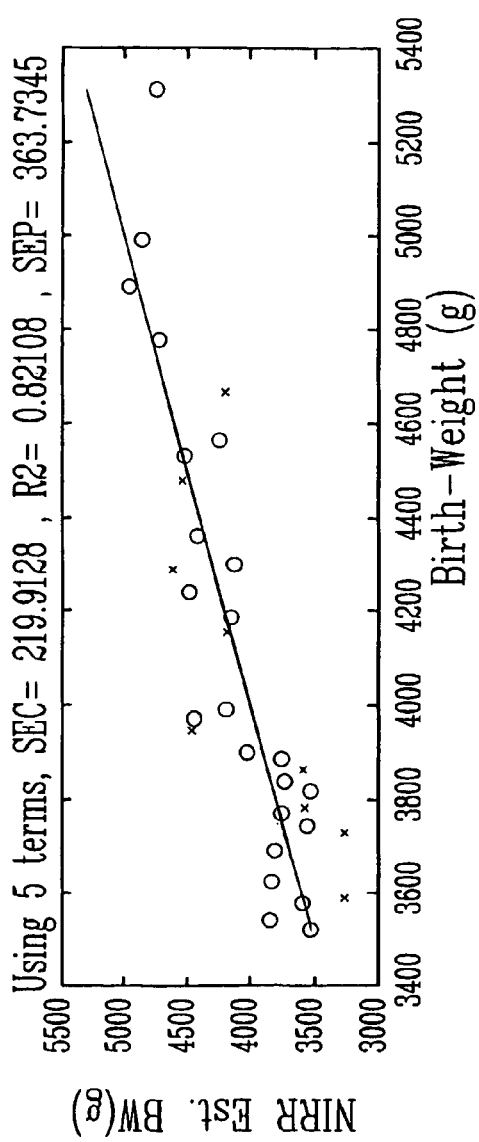
FIG. 1d illustrates the correlation fit between estimated birthweight and actual birthweight for the sample population for the lower range of birthweight ranging from 1 kg to 3.5 kg.
Figures 1E, 1F:
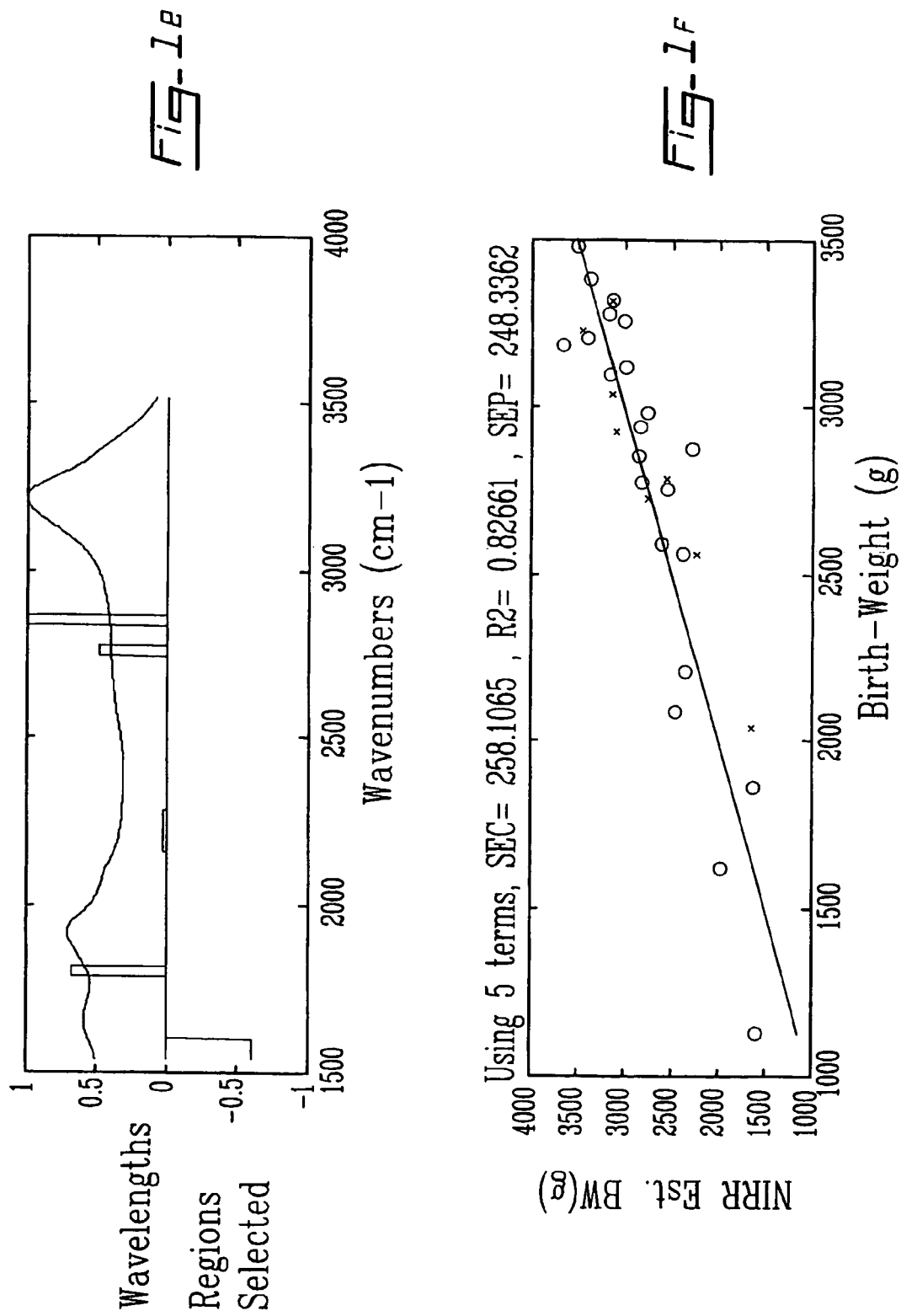
FIG. 1e illustrates the typical spectrum and wavelength regions selected for birthweight estimation using NIR Raman measurement of amniotic fluid for the higher range of birthweight ranging from 3.5 kg to 5.3 kg.
FIG. 1f illustrates the correlation fit between estimated birthweight and actual birthweight for the sample population for the higher range of birthweight ranging from 3.5 kg to 5.3 kg.

Three separate calibrations were made for estimating birthweight from the amniotic fluid RAMAN Spectra. First, spectra associated with all of the samples were used to estimate the birthweight. The results are shown in FIG. 1b. Estimation of birthweight within 500 grams for all sample were achieved. Significantly better results were obtained when the samples were subdivided into groups from <3500 grams and >3500 grams. Results of these two calibrations are shown in FIGS. 1d and 1f. As can be seen, estimations with approximately 200 grams error were found with only one outlier for each group. This is significantly better than any current method.

Second and Third Embodiments—In Situ Probe Including Optical Spectrometer

In the second embodiment, endo-vaginal spectral measurements are taken at the time of routine ultrasound which ranges from 2-5 times during the course of pregnancy. Early measurements present the opportunity for therapeutic or nutritional intervention. However, sensitivity of early gestational measurements may be reduced by the thickness of cervical tissue (~4 mm). In contrast, endo-vaginal measurements made later in pregnancy provide less interference from cervical tissue (<1 mm), as it thins throughout pregnancy, but there is less opportunity for medical intervention. It will be appreciated that ultrasound images of the amniotic sac may be used to help arranging the probe to direct or confirm that the probe will measure the amniotic fluid without interference of the fetus. If desired, the optical spectrometer may be incorporated into an ultrasound endo-vaginal probe.

The spectral regions which are critical in birth weight prediction for in situ measurements, in particular for estimations of IUGR and macrosomia can be expected to be slightly different from those obtained in the above described ex vivo, frozen samples due to intervening tissue, temperature and AMF pH. The specific regression model developed at different gestational time-points is to be compared to "gold" standard measurements obtained by ultrasound.

A regression relationship can be found between Raman spectra and birth weight using endo-vaginal NIR measurements. Likewise, the optical attenuation spectrum in the NIR or IR range can also be measured and correlated for predicting birthweight, and in accordance with the present invention other medical conditions. Raman scattering measurements provide good analytical information about amniotic fluid, however, optical attenuation or absorption measurements are expected to be more efficient in cases where measurement is to be done in situ and the depth of measurement of the amniotic fluid may render Raman measurements more difficult.

Figure 2:
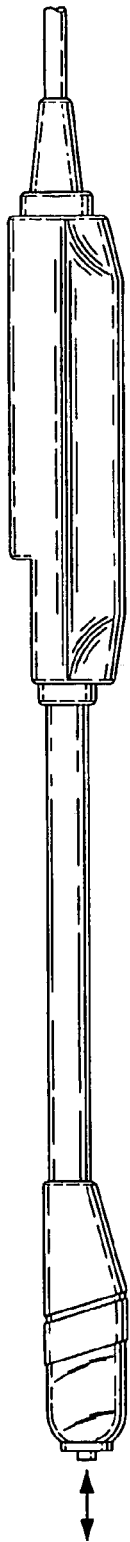
FIG. 2 illustrates an endo-vaginal optical Raman spectrometer operating at the NIR or IR range.

As shown in FIG. 2, the probe has a tip with an optical source and an optical detector. In the presently preferred embodiment, optical fibers relay light between a remote source and detector to the tip, although integration of a suitable source and detector into the probe tip is alternatively desirable.

Figure 3:
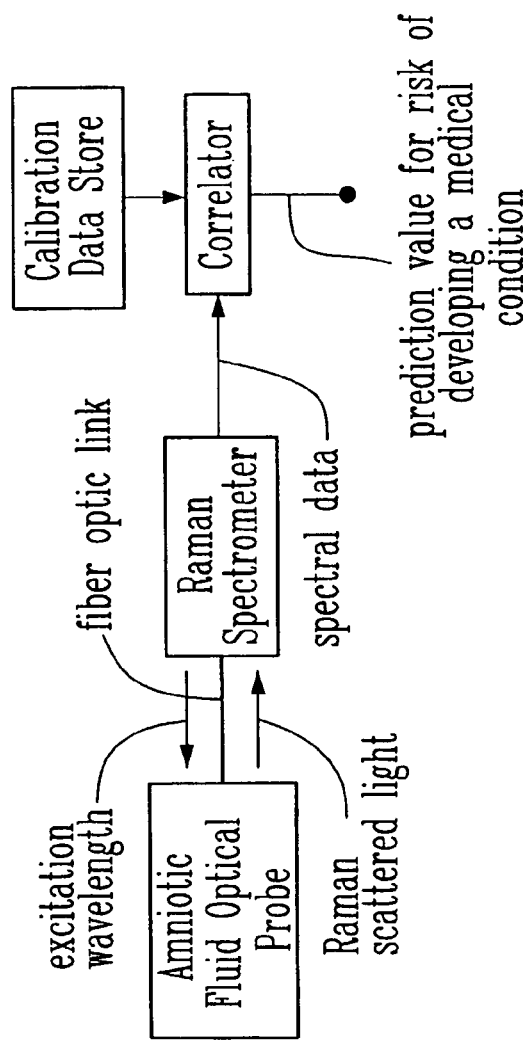
FIG. 3 is a block diagram of the apparatus according to the embodiment of FIG. 2.

As shown in FIG. 3, the optical probe is operatively connected to a spectrum analyzer that control the optical source or sources and detector or detectors to obtain the desired spectral information. As stated, such analyzer is a Raman scatter analyzer. The resulting spectrum data is received by a correlator that calculates a medical condition risk value based on calibration data that specifies how the spectral information is to be correlated to the risk value. It will be appreciated that either additionally or alternatively, the correlation may be performed to determine a value for concentration of a biochemical marker or other constituent of the amniotic fluid.

Figure 4:
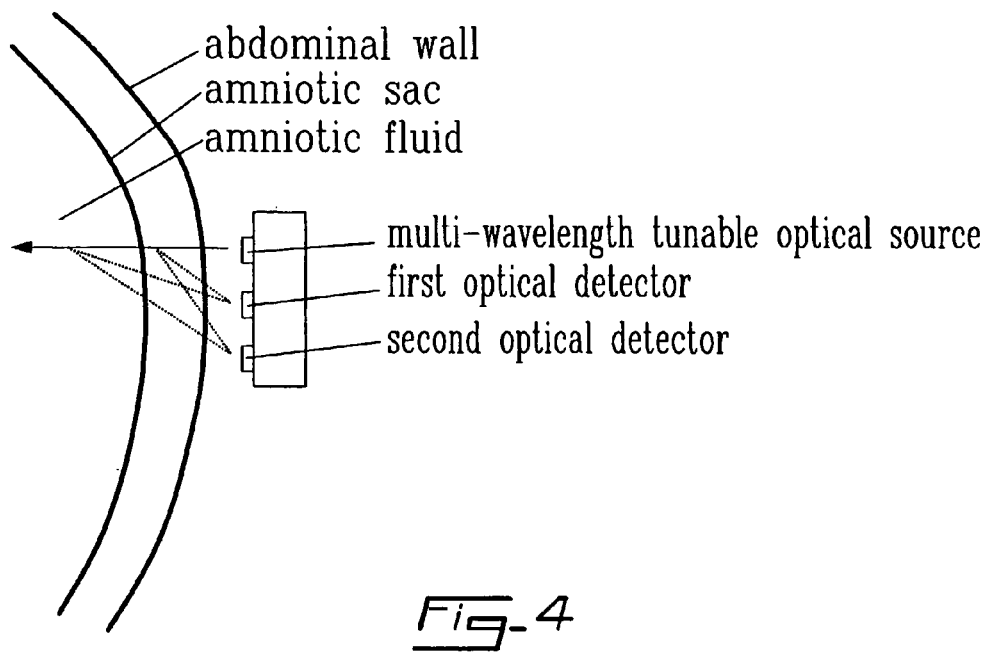
FIG. 4 is illustrates schematically an abdominal probe using an optical absorption spectrometer.
Figure 5:
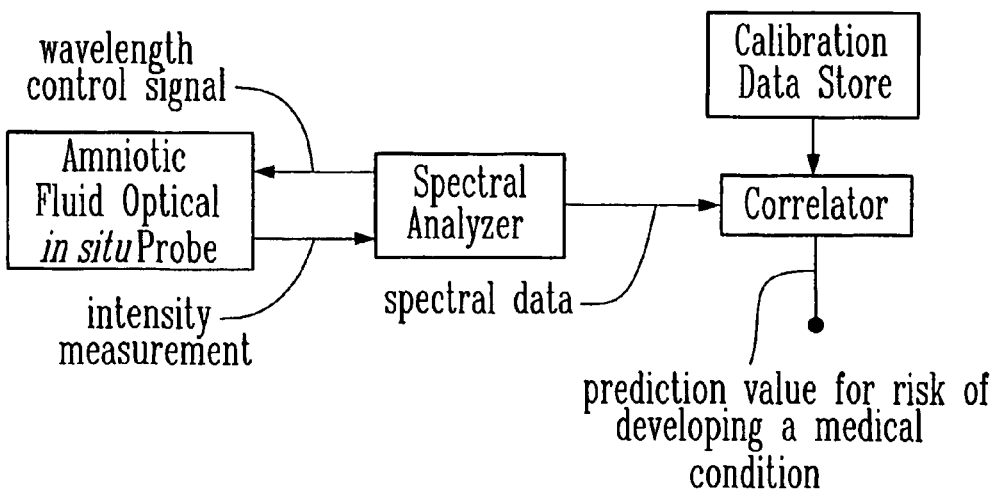
FIG. 5 is a block diagram of the apparatus according to the embodiment of FIG. 4.

In the third embodiment, shown in FIGS. 4 and 5, the probe to be adapted would have a non-invasive tip with an optical source and two optical detectors. As illustrated, the first detector "sees" a significantly different pathlength through the tissue between near tissue and deeper tissue, while the second detector "sees" less path difference. Subtraction of intensity data measured by the two detectors can thus yield information about deeper tissue, namely the amniotic fluid. The probe is adapted to be in optical contact with abdomen of the patient. In the case of an endo-vaginal probe, the device of FIG. 4 may also be desirable, however, the depth of the tissue or fluid to be measured is not as great, and thus the separation between first and second detectors need not be as great.

More specifically, in the case of a NIR-Raman system suitable for endo-vaginal measurements, a commercially available NIR-Raman system available from Ocean Optics may be adapted for the amniotic fluid measurements. The laser for the system can be a low power (50 mW) laser at 785 nm. Choice of the lower wavelength as compared to the 1064 nm used in the first embodiment is desirable since scattering is proportional to $\lambda^{-4}$ and will allow low optical power to be used for the non-invasive, in situ measurements. Likewise, this near infrared region will readily transmit through the cervical tissue expected in the measurements. The detector for the Raman spectrometer is a high sensitivity cooled CCD detector which provides a robust system for portable use. Our previous measurements suggest that relatively low resolution Raman spectra are sufficient for regression modeling of birth weight. Adjusting the entrance slit for the spectrograph provides a convenient means to optimize resolution and signal intensity for the in situ measurements. From our preliminary measurement, in vivo spectral acquisitions are expected to take approximately 3 minutes.

Both laser excitation and Raman scattering are transmitted to the patient by means of custom optical fiber bundles. The bundle consists of separate illumination and collection fibers which are focused to the same location in the tissue. We have shown that this confocal optical arrangement can be used to isolate precise locations in tissue for three dimensional quantitative measurement. At the distal end of the illumination fiber a small short wavelength pass, optical filter, is placed to remove unwanted scattering from the illuminating fiber. A second long wavelength pass filter is placed in front of the collection fiber to isolate the Raman shifted signal transmitted to the spectrograph. The diameter of the fiber bundle is less than 2 mm. The confocal optical probe is only 2 mm by 5 mm at the ultrasound scan head.

The fiber bundle is attached to a low cost ultrasound imaging system equipped with an endo-vaginal ultrasound scan head (Medison A-600) so that in vivo sampling locations can be determined. Using mechanical indents on the endo-vaginal probe, the fiber optics are clipped with Teflon retaining rings to maintain a known sampling location. In patients, condoms are slipped over the ultrasound/optical probe to provide a sterile environment. Location of spectral acquisition is determined using a tissue phantom. In addition to directing the location of spectral measurements, endo-vaginal ultrasound images will provide information about the geometry of the uterus and the membrane which will be useful for comparisons of the spectra. In addition to construction and calibration of the system with known composition samples, spectra of the purified constituents present in significant quantities in amniotic fluid can be used to provide reference spectra for the constituents so that comparisons between the spectral regions used in the regression can be made.

It will be appreciated that while the vaginal probe embodiment described above is intended for use in women, however, it will be appreciated that probes can be adapted for use in other mammals.

It will also be appreciated that non-optical analytical tools may likewise be used to gather information in situ about the composition of amniotic fluid that can be correlated to medical condition risk. For example, MRS can give detailed analytical information about chemical composition. Physical parameters of amniotic fluid, such as viscosity that can be measured in situ by ultrasound, may also be used either alone or in combination with other optical or non-optical analytical tools to determine risk or measure one or more biological markers. The amniotic fluid constituents that vary as a function of predicted birth weight are believed to affect viscosity, and thus correlation between viscosity and birth weight is expected.

In the case of optical spectrometry, the suitable wavelength region is roughly between 200 nm to 400 μm. Dried samples of amniotic fluid can be analyzed throughout this range, while whole samples ex vivo, or amniotic fluid in situ is analyzed using wavelengths that are not unduly absorbed by any intervening tissue or the fluid itself. For example, water absorbs heavily in the range of 2 μm to 50 μm, and the presence of water in the amniotic fluid essentially prevents this range from being used for in situ measurements.

Fourth and Fifth Embodiments—Monitoring of Gestational Diabetes Mellitus (GDM) Using Repeated Non-Invasive Amniotic Fluid Analysis Our study goals were fourfold: 1) to describe the prevalence of GDM in a population of older women undergoing routine amniocentesis for genetic testing and at higher risk because of age; 2) to show if elevations in amniotic fluid (AF) glucose, insulin or insulin-like-growth-factor binding protein (IGF BP) 1 pre-existed at the time of routine amniocentesis (range 12-22 wks) in those women diagnosed at 24-28 wks with GDM; 3) to establish, using multiple regressions, if an association with these amniotic fluid indices and later GDM diagnosis existed; and 4) to demonstrate, using probability maps, specific amniotic fluid concentrations for glucose, insulin and IGF BP 1 that were predictive of increased risk for GDM.

Design, Recruitment and Consent: From 1998-2002, pregnant women undergoing routine amniocentesis at St Mary's Hospital Center in Montreal Canada were approached to participate in this prospective study. Signed consents allowed researchers to obtain amniotic fluid from Montreal Children's Hospital following genetic testing and to access the maternal medical charts. Applying inclusion (singleton pregnancy) and exclusion criteria (multiple births, genetic anomalies) resulted in 1008 participants. Medical chart review provided information on GDM status, maternal age, prepregnancy weight and height, ethnicity, parity, and smoking (n=888-928), fetal weights estimated by ultrasound at 25 wks (n=70) and at 35 wks (n=149) and infant birth weight, gender and gestational age (n=928). Gestational age was based on physicians' estimates using LMP and uniform hospital protocols. Completeness of each data subset depended on availability of information in medical charts and on questionnaires. Ethics approval was obtained from Institutional Review Boards of McGill, Montreal Children's Hospital and St Mary's Hospital Centre.

Biochemical Analysis. Amniotic fluid samples, stored at −80° C., were analyzed for glucose, insulin and IGF BP 1. Insulin (n=718) was analyzed using the Beckman Access ultrasensitive assay system, a one step immunoenzymatic assay that added a monoclonal anti-insulin conjugate, an antibody coated paramagnetic particles, and a chemiluminescent substrate to the reaction vessel. Insulin is measured to within 0.03-300 ul pmol/L. Glucose (n=662) was analyzed after adapting Abbott Laboratories (North Chicago, Ill.) assay kit (No. 6082) for use with a micro plate reader and IGFBP1 (n=876) by ELISA using Diagnostics Systems Laboratories Inc (DSL kit 10-7800, Webster, Tex.).

Figure 6:
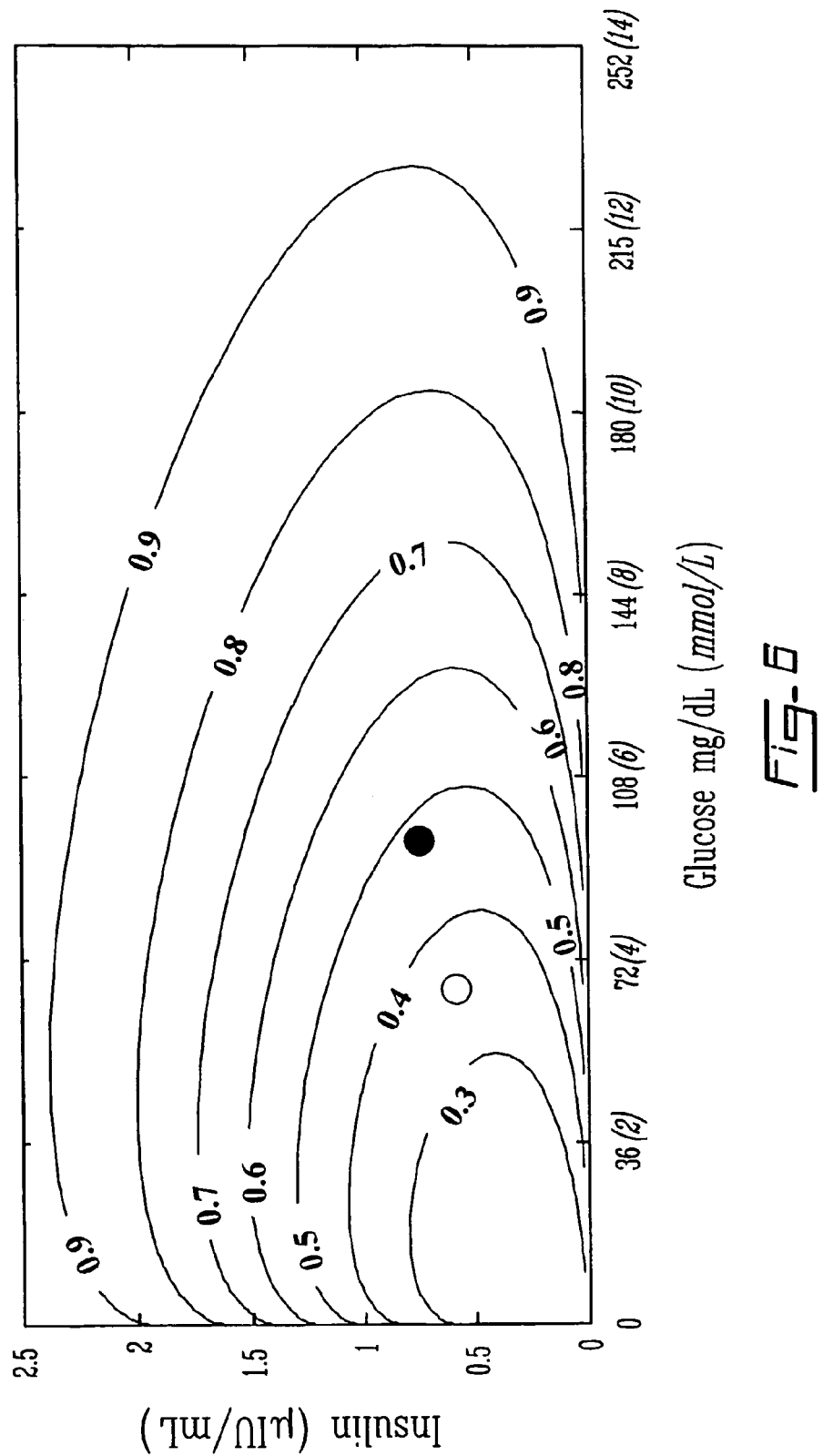
FIG. 6 is a probability contour plot of developing gestational diabetes mellitus (GDM) as a function of glucose level in amniotic fluid (X-axis) and insulin (Y-axis)
Figure 7:
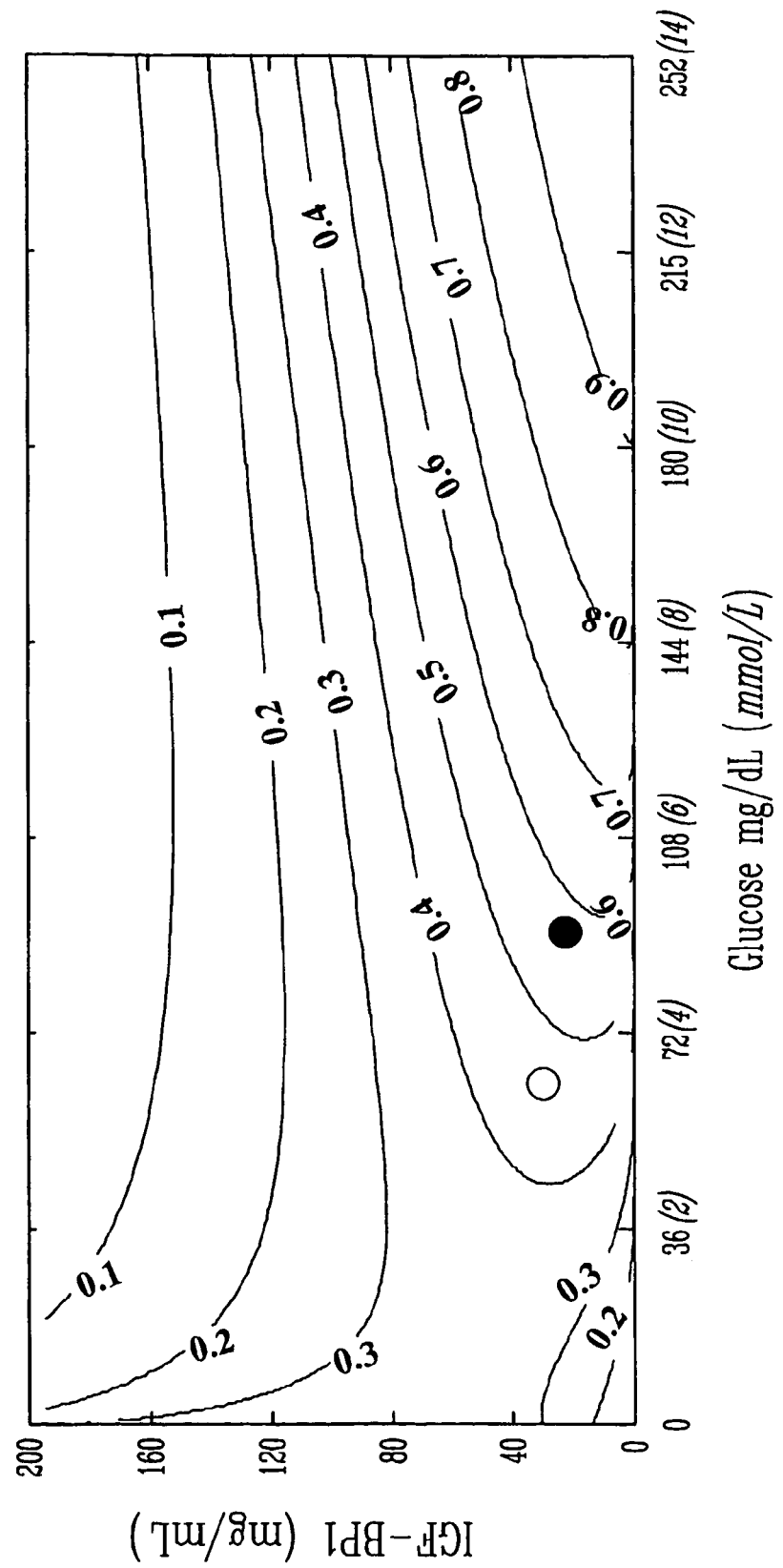
FIG. 7 is a probability contour plot of developing gestational diabetes mellitus (GDM) as a function of glucose level in amniotic fluid (X-axis) and intrauterine growth factor binding protein 1 or IGF-BP1 (Y-axis)

Statistical Analysis: All data analysis were performed using SAS (Version 8.02, SAS Inc., Cary, N.C.) with $P<0.05$ set as the minimum for statistical significance. All non-normally distributed data were transformed using square root: prepregnancy weight, BMI, ethnicity, parity, amniocentesis week, smoking, infant birth weight, 35-week fetal weight, and amniotic fluid glucose, insulin and IGF-BP 1. Biochemical comparisons between GDM and non-GDM mothers included as covariates maternal prepregnancy BMI, ethnicity, parity and week that amniocentesis was performed. Multiple regression for GDM and birth weight as dependent variables and with previously established predictors included in the models were also verified using forwards and backwards regressions. Due to co-linearity among IGF BP1, insulin and glucose, each was included in separate regression models. Data for both GDM and non-GDM mothers were separately modeled using a mixture of Gaussian distributions that employed a program written in Matlab V6.1 (Mathworks, Inc) called Bayesnet by Ian McNabbey of Cambridge University. A postpriori probability of development of GDM from amniotic fluid biomarkers for insulin and glucose was calculated using a Bayesian weighting of the Gaussian profiles determined from the measured data. A contour map of the probability of development of GDM was then determined for variations in IGF-BP1 and insulin as related to glucose in the AF, as shown in FIGS. 6 and 7, respectively.

Population characteristics: Comparisons between our GDM and non-GDM sub-populations showed that GDM mothers were shorter, had higher prepregnancy weights and BMIs; 54% of our GDM mothers were overweight or obese while only 26% of non-GDM mothers were. Average birth weight was 3396±19 g in our healthy non-GDM mothers verses 3515±52 g in our GDM mothers. However, only 16% of GDM offspring and 12% of non-GDM offspring were >4000 g; using birth-weight-percentiles that correct for gender and gestational age, 23% of infants born to GDM mothers were >90% (LGA) while only 10% were LGA in our non-GDM population. Both classifications resulted in 3-4% of our GDM mothers giving birth to either IUGR or SGA infants. Fetal weights did not different by 25 wks but were 134 grams higher by 35 wks in GDM mothers. Moreover, at 35 wks, gestational age ($\beta$-coefficient ($\beta$)=215 g) and GDM ($\beta$=54 g; p=0.0450), but not BMI, smoking and infant gender, entered as independent predictors of fetal weight. This difference decreased to 119 grams by term, at which time, GDM entered ($\beta$-coefficient=165 g) along with smoking ($\beta$=−111 g), infant gender ($\beta$=124 g) and gestational age ($\beta$=135 g), and prepregnancy height and weight ($\beta$=750 and 7.50 respectively) as independent predictors of infant birth weight. The occurrence of GDM was 12% in our study population (n=928) of older mothers (37.8±0.1 yrs, 26-45 yr).

Biochemical Measurements: Concentrations of amniotic fluid glucose were higher while amniotic fluid IGF BP1 was lower in GDM vs. non-GDM mothers despite inclusion of BMI, ethnicity, parity, and amniocentesis week; interestingly amniotic fluid insulin no longer differed upon inclusion of these covariates. However, we found that all three amniotic fluid biochemicals entered as independent predictors for GDM, but only amniotic fluid IGF-BP 1 entered for birth weight and as a negative predictor. Using probability maps to visualize the risk of GDM, we were able to show that if either amniotic fluid glucose or insulin were high and the other concentration low in amniotic fluid, the risk for GDM exceeded 90%. Moreover, low amniotic fluid IGF BP 1 in the presence of a high glucose was also associated with >90% risk for GDM.

Our study explored the possibility that concentrations of amniotic fluid glucose, insulin and IGF BP 1 might already be high in women subsequently diagnosed with GDM, raising the possibility that these amniotic fluid constituents might act as early prognosticators for GDM. Our findings are revolutionary because we 1) demonstrated that high AF glucose and low IGF BP1 were associated with the later GDM diagnosis in women of varying BMI categories and offspring with varying birth weights and 2) were able to predict by 15 wks gestation, using probability plots, the risk for subsequent diagnosis of GDM for each AF glucose, insulin and IGF BP 1 concentration. Our GDM risk profile assessment using amniotic fluid samples obtained at the time of routine amniocentesis for genetic testing preceded current screening and diagnosis protocols by 10 wks, was based on the presence of high amniotic fluid insulin and glucose concentrations measured earlier in pregnancy and demonstrated that the developing fetus was being exposed to a glucose-enriched environment much earlier in GDM moms. Current protocols screen for higher maternal BMI, and effectively attempt to minimize higher birth weights by decreasing fetal abdominal circumference, macrosomia, obesity, in GDM offspring, but do nothing to diminish the fetopathy associated with earlier in-utero glycation and glycosylation of proteins, reported to exist by the third trimester in GDM mothers. With elevations in amniotic fluid glucose much earlier in pregnancy, fetal damage may be greater than previously expected given that amniotic fluid glucose can diffuse through the unkeratinized fetal skin until 20-24 wks, and which could lead to exposure of the developing fetal pancreas to early elevations in amniotic fluid glucose that predispose to an increased risk of beta cell exhaustion later in life and increase risk of adult disease, with higher BMI and greater risk of developing diabetes and GDM later in life.

Our population had a prevalence of GDM of 12%. This incidence is higher than that reported by CDA for a multiethnic population including aboriginals (i.e. 8-18%) and greater than that reported by the ADA (7%). This is not surprising given that the average age of our mothers undergoing routine amniocentesis for genetic testing was greater than that indicated as a risk factor by both the CDA and ADA (i.e. >25 and >35 yrs), but it does provide the first report of the incidence in this high-risk population of older women. Noteworthy, was the higher percentages of Asians in the GDM population as compared to the non-GDM population (37% vs. 18%); however, this observation supports other reports of a higher prevalence of GDM in Asians. Interestingly, GDM occurred as frequently in women with BMI less than 25 as in those with BMI greater than 25. Since traditional screening approaches emphasize high prepregnancy weight as a risk factor, our data could offer some insight as to why GDM is being underdiagnosed if as many normal and underweight individuals are as susceptible. Interestingly, most women gave birth to non-macrosmic offspring where the presence of GDM was associated with a 165 gram increase in birth weight. Traditionally the Pedersen hypothesis has associated increased birth weight with fetal hyperglycemia and large-for-gestational-age infants, but we also observed that GDM mothers were just as likely to give birth to SGA and AGA. Otherwise, our multiethnic population was non-smoking, with an incidence of IGUR lower than that in the normal population but with an incidence of AGA and macrosomia similar to the Canadian and US populations at large.

GDM is currently diagnosed between 24-28 wks. As stated our study revealed that AF glucose was already elevated in our GDM sub-population by 15 wks gestation. Some studies had previously suggested that maternal fasting and 2 h plasma glucose levels were positively associated with birth weight and that glucose passes freely across the placental barrier via facilitated diffusion, while another study reported that AF insulin was a better predictor than AF glucose of impaired maternal glucose intolerance; one study actually showed that AF glucose was not associated with fetal hyperinsulinism prior to 23 wks gestation. Our amniotic fluid study, which used a much larger sample size and controlled for established confounders, showed in a series of multiple regressions that amniotic fluid glucose and insulin were associated with GDM; birth weight was not predicted by either most likely because amniotic fluid insulin measured early in pregnancy is not the primary growth factor during early pregnancy but may accumulate during this time and act later in pregnancy. As for glucose, it predicted GDM but failed to predict birth weight most likely because GDM mothers, who had been treated, gave birth to infants with a wide range of birth weights. Importantly, however, with the construction of probability maps, the complexity of the AF glucose and insulin to predict GDM was evident. Probability contour maps demonstrated that the relationship clearly was not linear and if either amniotic fluid glucose or insulin were high and the other concentration was low, the risk for GDM exceeded 90%. Moreover the contour line for each risk profile was non-linear. Therefore what appears to be most important is for a dissociation to exist between the glucose and insulin values. Wide discrepancies between the two are more indicative of future emergence of GDM demonstrating that both fetal hyperinsulinism and elevations in amniotic fluid glucose are predictive of subsequent development of GDM.

Another interesting predictor of GDM was low amniotic fluid IGF BP 1 in the presence of a high glucose, which was associated with >90% risk for GDM. Previously IGF BP 1 was inversely associated with birth weight, but we showed using a much larger sample size that lower IGF BP 1 was associated with a 54 g increase in fetal weight by 35 wk and a 164 g increase in birth weight at term. Previous studies have shown this to be due either to higher levels of growth hormone and/or increased levels of circulating IGF 1 or to increased insulin secondary to increased food ingestion, both of which inhibit placental IGF BP 1 production. Increased active IGF 1 would stimulate greater fetal growth during later gestation, and may be responsible for the already established greater fetal weight by 35 wk in GDM vs. non-GDM offspring.

In conclusion we showed that high AF glucose, insulin and low IGF BP 1 predicted GDM and where GDM positively predicted infant birth weight. Because our results convincingly demonstrate that the developing fetus of GDM mothers is already exposed to a 'diabetogenic risk profile' in advance of current GDM diagnosis, earlier screening and intervention is warranted in order to minimize in utero fetal damage. Additionally, an over-emphasis on BMI as a screening criterion may be responsible for much of the GDM under diagnosis, since we observed almost 50% of our GDM mothers with BMI <25 and many of the infants were not born large for gestational age.

Figure 8:
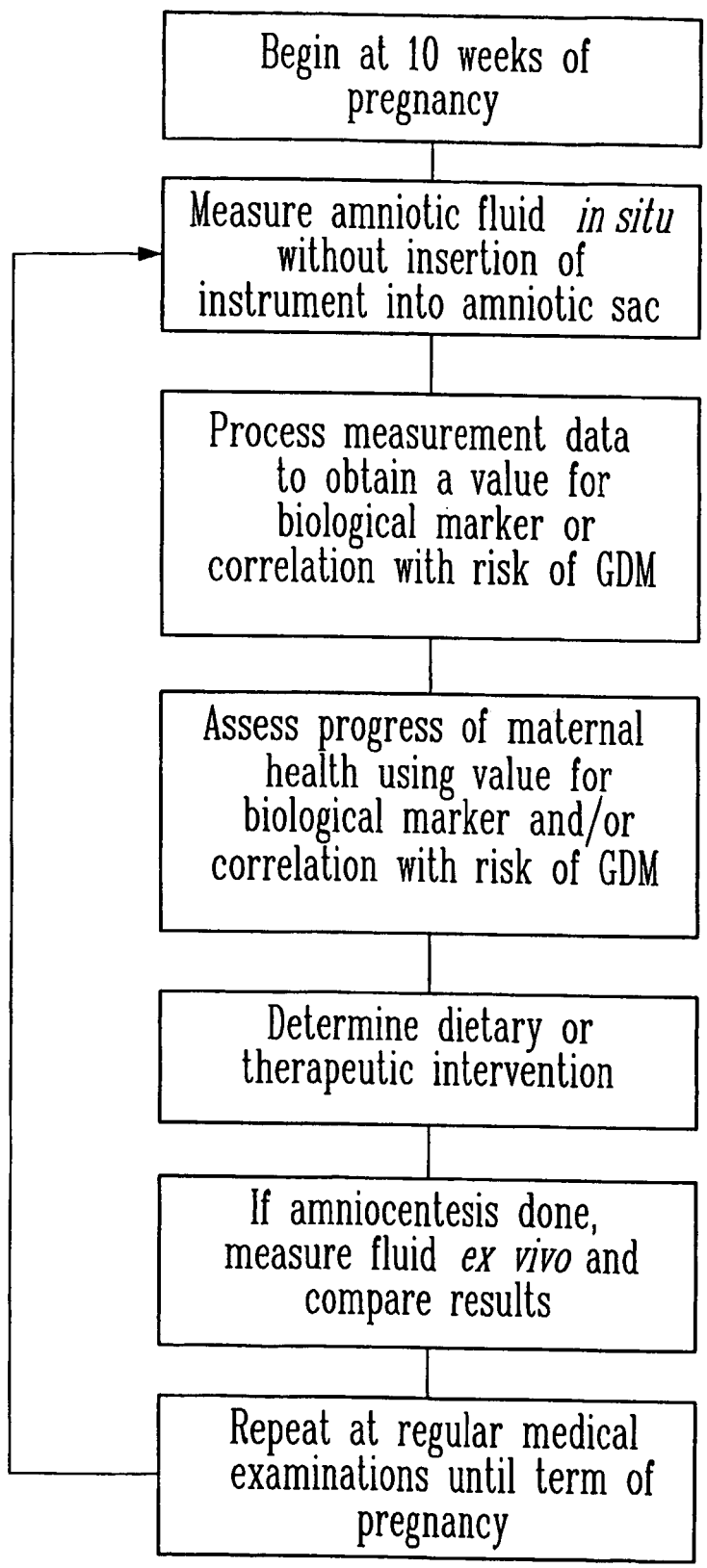
FIG. 8 is a flow chart illustrating the method of treating GDM according to the fifth embodiment.

In the fifth embodiment, the medical condition of GDM is followed using the invention by repeating measurements of amniotic fluid during pregnancy to monitor health and the impact of dietary and/or therapeutic intervention. The method is illustrated in FIG. 8. It will be appreciated that the combination of in situ measurements with data obtained during amniocentesis is optional, although the confirmation may be reassuring to physicians not used to interpreting or relying on in situ analysis of amniotic fluid. Likewise, while the invention allows for in situ measurement that can be performed before 12 weeks of pregnancy in women, as illustrated at 10 weeks, and thus well before amniocentesis could safely be performed, a physician could also choose to start monitoring maternal health according to the invention at a later time during pregnancy. While this embodiment is illustrated with the example of GDM, it will be appreciated that it equally applies to monitoring fetal health, as in the case of birthweight. Changing diet in the mother is recognized as being able to influence ultimate birthweight, and the symptoms of GDM risk. It is believed that early detection of risk of developing GDM, and consequently, early change of diet will be efficient in reducing actual outcome of developing GDM. Exercise and pharmaceutical intervention may also be applied in accordance with medical guidelines.

The invention claimed is:

1. A method comprising:
   a) providing a Raman spectrometer that operates in the near-infrared range;
   b) arranging the spectrometer with respect to an amniotic sac of a pregnant mother to acquire a spectrum of amniotic fluid in situ without insertion of any instrument into said amniotic sac;
   c) using said spectrometer to acquire said spectrum; and
   d) processing said spectrum to predict a risk of developing a medical condition in at least one of said pregnant mother and her offspring based on a predetermined correlation between spectra of amniotic fluid and the likelihood of developing said medical condition.

2. The method as claimed in claim 1, wherein said arranging comprises directing said spectrometer to analyze said amniotic fluid through an abdominal wall.

3. The method as claimed in claim 1, wherein said arranging comprises directing said spectrometer to analyze said amniotic fluid through a cervix.

4. The method as claimed in claim 3, further comprising acquiring ultrasound images of the amniotic sac during said arranging to direct or confirm that said spectrometer will acquire said spectrum without interference of said pregnant mother's offspring.

5. The method as claimed in claim 1, further comprising:
   e) determining at least one of a dietary intervention and a therapeutic intervention in response to finding that at least one of said pregnant mother and her offspring risks developing said medical condition.

6. The method as claimed in claim 5, wherein steps a) to e) are repeated during said pregnant mother's pregnancy.

7. The method as claimed in claim 5, wherein said pregnant mother is human, and steps a) to e) are first performed before 12 weeks of said pregnant mother's pregnancy.

8. The method as claimed in claim 7, wherein an amniocentesis is performed after steps a) to e) are first performed.

9. The method as claimed in any one of claims 6 to 8, wherein steps a) to e) are repeated at least three times during said pregnant mother's pregnancy.

10. The method of claim 1, wherein the medical condition is birthweight.

11. The method of claim 1, wherein the medical condition is gestational diabetes mellitus.

12. A method comprising:
   a) providing a Raman spectrometer that operates in the near-infrared range;
   b) using said spectrometer to acquire a spectrum of amniotic fluid of a pregnant mother, wherein said optical spectrometer is arranged with respect to the pregnant mother's amniotic sac to acquire a spectrum of said amniotic fluid in situ without insertion of any instrument into said amniotic sac and wherein the amniotic fluid is analyzed without processing said fluid to separate or concentrate its components; and
   c) processing said spectrum to predict a risk of developing a medical condition in at least one of said pregnant mother and her offspring based on a predetermined correlation between spectra of amniotic fluid and the likelihood of developing said medical condition.

13. The method as claimed in claim 12, wherein said arranging comprises directing said spectrometer to analyze said amniotic fluid through an abdominal wall.

14. The method as claimed in claim 12, wherein said arranging comprises directing said spectrometer to analyze said amniotic fluid through a cervix.

15. An apparatus for predicting a risk of developing a medical condition in at least one of a pregnant mother and her offspring, the apparatus comprising:
- a Raman spectrometer that operates in the near-infrared range adapted to acquire a spectrum of amniotic fluid from said pregnant mother;
- an optical coupler adapted to arrange said optical spectrometer with respect to said pregnant mother's amniotic sac to acquire a spectrum of said amniotic fluid in situ without insertion of any instrument into said amniotic sac; and
- a processing unit for processing said spectrum to predict a risk of developing a medical condition in at least one of said pregnant mother and her offspring based on a predetermined correlation between spectra of amniotic fluid and the likelihood of developing said medical condition.

16. The apparatus as claimed in claim 15, wherein said coupler is adapted to arrange said spectrometer to analyze said fluid through an abdominal wall.

17. The apparatus as claimed in claim 15, wherein said coupler is adapted to arrange said spectrometer to analyze said fluid through a cervix.

18. The apparatus as claimed in claim 15, wherein said coupler is adapted to operate in contact with said pregnant woman in a position near said amniotic sac.

19. The apparatus as claimed in claim 15, wherein said optical coupler is comprised within an endo-vaginal probe.

20. The apparatus as claimed in claim 19, wherein said endo-vaginal probe also functions as an ultrasound device.

21. The apparatus as claimed in claim 15, wherein said optical coupler comprises an optical source and two optical detectors.

* * * * *